United States Patent [19]

Takematsu et al.

[11] 4,013,449
[45] Mar. 22, 1977

[54] METHOD OF CONTROLLING WEED GROWTH IN A PADDY FIELD

[75] Inventors: Tetsuo Takematsu; Makoto Konnai, both of Utsunomiya; Takayuki Isogawa, Tokyo; Koshiro Kodama, Noshiro, all of Japan

[73] Assignee: Hodogaya Chemical Co., Ltd., Tokyo, Japan

[22] Filed: July 14, 1975

[21] Appl. No.: 595,801

[30] Foreign Application Priority Data

July 12, 1974 Japan ................................ 49-79091

[52] U.S. Cl. ...................................... 71/106; 71/87; 71/97; 71/100; 71/118
[51] Int. Cl.$^2$ ............................................ A01N 9/24
[58] Field of Search .............................. 71/118, 106

[56] References Cited

UNITED STATES PATENTS

| | | | |
|---|---|---|---|
| 3,134,666 | 5/1964 | McRae | 71/118 |
| 3,154,398 | 10/1964 | McRae | 71/118 |
| 3,425,820 | 2/1969 | Kawai et al. | 71/118 |
| 3,930,838 | 1/1976 | Pellegrini et al. | 71/118 |

FOREIGN PATENTS OR APPLICATIONS

| | | | |
|---|---|---|---|
| 43-8032 | 3/1968 | Japan | 71/106 |
| 4,411,918 | 5/1969 | Japan | 71/106 |

OTHER PUBLICATIONS

Tao, "Control of *Schoenobius incertallas* etc.," (1963) CA 60, p. 8578 (1964).

*Primary Examiner*—Glennon H. Hollrah
*Attorney, Agent, or Firm*—Oblon, Fisher, Spivak, McClelland & Maier

[57] ABSTRACT

A method of weeding annual weeds in a flooded paddy field comprising applying more than 15 g of 3,4-dichloropropionanilide and 0.2 -2.5 g β-naphthyl-N-methyl carbamate per 1 are (100 m$^2$) without a foliage treatment.

7 Claims, No Drawings

METHOD OF CONTROLLING WEED GROWTH IN A PADDY FIELD

BACKGROUND OF THE INVENTION

1. Field of the Invention

The present invention relates to a method of controlling annual weeds in a flooded field by effective application of a selective post-emergence herbicide of 3,4-dichloropropionanilide in a flooded condition.

2. Description of the Prior Art

Heretofore, it has been known that 3,4-dichloropropionanilide (DCPA) is a herbicide for foliage treatment which has no phytotoxicity to rice plants and is effective in controlling gramineous weeds, especially barnyard grass, and also young broadleaf weeds. Accordingly, DCPA has been widely used as a herbicide in paddy fields. However, it is also well-known that the herbicidal activity of DCPA is decreased in the presence of water, whereby desirable herbicidal effects cannot be achieved when the fields are in a flooded condition. Furthermore, in order to effectively apply DCPA, the surface of the field should be exposed before application and the soil surface should be maintained in an unwatered state for 2 to 3 days. This requirement of water management before and after treatment and the attendant control of the water supply which is required cause inconveniences in the field application of DCPA. Accordingly, DCPA has been applied to rice growing areas in upland fields, in upland nursery beds, in paddy fields after the water has been drained and in directly seeded paddy fields after the water has been drained. In the direct-seeding culturing of paddy rice under water-drained field conditions, the field is later flooded. Accordingly, 97% of the world's rice has been cultured in paddy fields, of which 30 – 40% are ill-drained, i.e., where surface drainage cannot be attained. Consequently, notwithstanding the outstanding phytophysiological selectivity of DCPA to rice, the contribution of DCPA to the world's rice cropping industry is small.

In Japan, transplanting culturing has been used in most fields. Accordingly, the application of DCPA has been quite limited. However, there is no other foliage-treating type herbicide which has selectivity to barnyard grass without phytotoxicity to rice plants. Accordingly, several studies have been undertaken to develop techniques for applying DCPA to fields in flooded conditions, as disclosed in Japanese Patent Publications No. 2080/1967, No. 1490/1968 and No. 16934/1969. In these cases, DCPA is used as the main component and certain auxiliary ingredients are added so as to impart a herbicidal activity in the presence of water. Japanese Patent Publication No. 2080/1967 discloses the combination of DCPA and one of certain phenyl or naphthyl carbamates, thiophosphates or trialkyl tin compounds. By using the proper proportions, the composition is used as a contact herbicide for foliage treatment of paddy fields in a flooded condition. This method has been considered to be effective. However, the phytophysiological selectivity toward barnyard grass versus rice plant is remarkably decreased by the addition of the second ingredient as compared with the application of DCPA alone. Accordingly, the field and rice plant conditions under which the composition is effective are quite limited. This is a significant disadvantage in practical application. The conclusion has been reinforced in several studies of the method's efficacy. The method of Japanese Patent Publication No. 2080/1967 also has other disadvantages. It has been found that phytotoxicity is caused by DCPA when certain commercial carbamate or organic phosphorus insecticides are applied within 10 days of the application of DCPA. This is a serious disadvantage for use of DCPA. Using the foliage treating method, it has been difficult to overcome these disadvantages. Accordingly, the invention of Japanese Patent Publication No. 2080/1967 has not been used in practice.

As the result of a series of studies, the composition of Japanese Patent Publication No. 16934/1974 has been registered and used in practice. The composition comprises DCPA and S-(4-chlorobenzyl)-N,N-diethylcarbamate as active ingredients.

The composition of Japanese Patent Publication No. 2080/1967 comprises DCPA and methyl-N-(3,4-dichlorophenyl)carbamate as active ingredients. In both cases, it has been necessary to apply more than 50 g per 1 are (100 m$^2$) to obtain satisfactory results.

A characteristic feature of all of these Japanese patent publications is the determination of suitable methods of application of DCPA. That is, it has been considered in the past that the herbicidal effect cannot be attained without spraying the composition of DCPA onto the stems and leaves of the plant (foliage treatment). In accordance with studies of methods of application of DCPA to plants in a flooded field, it has been found that the selective herbicidal effect of DCPA can be attained by dispersing certain selected second components in the flooding water. In accordance with this method, the herbicidal components are not directly contacted with the rice plants above the water surface. Accordingly, the phytotoxicity caused by subsequently applying an insecticide in the presence of DCPA can be remarkably decreased. However, these methods also have disadvantages. Firstly, the suitable leaf stage for controlling barnyard grass is 2 – 3 leaf stage or lower. However, it is desirable to be able to control barnyard grass in higher stages of leaf growth because of attendant labor savings. Secondly, in order to attain the herbicidal effect in flooded waters, a quite large amount of DCPA has to be applied in said methods. But this requirement is contrary to the latest theories of the technology of concern, and it is necessary to decrease the amount of DCPA to at least that of the foliage treatment.

In summary, then, two methods of application of DCPA have been used: foliage treatment or dispersal in the flooding water. But both have significant disadvantages. Consequently, it would be most desirable to find a second ingredient so as to improve the selectivity of the herbicidal effect on barnyard grass relative to rice plants (as in the selectivity of DCPA itself) and to increase the herbicidal activity of DCPA while overcoming the disadvantages of the present application methods.

SUMMARY OF THE INVENTION

Accordingly, it is an object of the present invention to provide a method of controlling weed growth in a flooded paddy field by effective application of DCPA without a foliage treatment.

Briefly, this and other objects of this invention, as will hereinafter become clear by the discussion below, have been attained by providing a method which comprises applying more than 15 g of 3,4-dichloropropionanilide (DCPA) having the formula

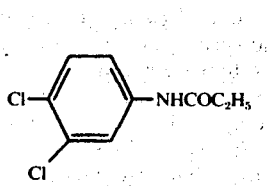

as a main herbicidal ingredient, and 0.2 – 2.5 g of β-naphthyl-N-methyl carbamate (β-NAC) per 1 are (100 m²) in a paddy field under flooded conditions without a foliage treatment. The ingredients may be applied simultaneously as a composition or in any desirable order.

DESCRIPTION OF THE PERFERRED EMBODIMENTS

The combination of the second ingredient of this invention with DCPA is disclosed in Example 2 of Japanese Patent Publication No. 2080/1967. However, as with the other compositions of that invention, the composition could not be applied in practice since only foliage treatment was used. The synergistic effect of β-NAC with DCPA with no foliage treatment was not found because the other compounds of the reference were considered to be equivalent to β-NAC. Thus, the method and results of this invention (with no foliage treatment) are unexpected and unobvious. The selectivity of the composition toward barnyard grass versus rice plants is improved by combining DCPA with β-NAC and applying no foliage treatment as compared with other known combinations and methods of application, and the phytotoxicity caused by an application of a commercial insecticide in conjunction with the herbicidal treatment can be remarkably decreased.

The compound β-NAC is an isomer of α-naphthyl-N-methyl carbamate (hereinafter referred to as α-NAC) which is used as an insecticide, but it has no insecticidal effect. In the method of this invention, the amount of DCPA should be more than 15 g/are, preferably 20–50 g/are, especially 25 – 35 g/are, and the amount of β-NAC should be 0.2 – 2.5 g/are, preferably 0.5 – 2.0 g/are, especially 1.0 – 1.7 g/are. The resultant herbicidal activity and phytotoxicity are not always the same, but depend on the nature of the plants treated and the environment of the area treated. When more than 40 g/are of DCPA is applied, the amount of β-NAC is relatively low, and when less than 40 g/are of DCPA is applied, the amount of β-NAC is applied so as to impart satisfactory herbicidal effects and to prevent phytotoxicity to the rice plants.

In the method of this invention, the active ingredients are dispersed into the flooded water. It is preferred to apply DCPA and β-NAC within 2 days of each other, preferably applying β-NAC first and then DCPA within 2 days. However, it is possible to apply them simultaneously if convenient, as in agricultural work. In accordance with tests, it has been found that the optimum effect can be attained by applying the composition of DCPA and β-NAC. More specifically, the method of this invention is to apply the active ingredients of DCPA and β-NAC by dispersing them in flooded water without contacting the stems and leaves (foliage) of the plants above the surface of the water. Accordingly, it is possible to scatter on the water surface a granular form of the composition which will not adhere to the rice seedlings. In the form of an emulsion or a wettable powder, the composition is supplied to the paddy field by introducing it into either a watering channel or a water inlet of the field. When the composition of this invention is applied by the foliage treatment, the selectively to barnyard grass versus rice plant is decreased and stable herbicidal effects cannot be expected.

In accordance with the method of this invention, it is possible to control barnyard grass in the four-leaf stage or lower. Accordingly, suitable times of application are prolonged as compared with other compositions which include DCPA. When the weeds are in water, effective herbicidal effects can be attained, without directly contacting the active ingredients to the stems and leaves (foliage) above the surface of the water. Accordingly, the depth of water in the paddy field can usually be in the range of about 3 – 10 cm, preferably about 3 – 6 cm.

The method of this invention can control not only barnyard grass but also annual weeds which are germinated after the transplantation of rice plants. The weeds controllable in the paddy field include barnyard grass; Umbrella sedge (*Cyperus Iria L*); Monochoria (*Monochoria vaginalis Presl*); Rotala indica Koehne; False pimpernel (*Lindernia pyxidaria Linnaeous*); Waterwort (*Elatine triandra Schkuhr*); Water clover (*marsilea polycarpa Hook et Grev*); Chara (*Chara vulgaris L*); algae; and Greater duckweed (*Spirodela polyrhiza Schleiden*). In order to control perennial weeds such as Spikerush (*Eleocharis acicultaris Romer et Schultes*), it is necessary to add a third ingredient or to apply another herbicide. The method of this invention can employ the composition in the form of an emulsion, a wettable powder, granules and the like. It is preferred to apply it as an emulsion because uniform dispersion of the active ingredients in the flooded water is desirable. However, it is convenient to apply it as granules because of easy handling.

The special characteristics of β-NAC used in the method of this invention will be illustrated as compared with α-NAC, an isomer thereof. It is well-known that α-NAC is an active ingredient used for controlling plant hoppers (Delphacidare) and leaf hoppers (Delocephalidae). In Japanese Patent Publication No. 2080/1967, α-NAC is disclosed as one of the additives. The physical properties and insecticidal activities of β-NAC and α-NAC are shown in Table 1.

TABLE 1

| Melting point | α-NAC 142° C | β-NAC 116–117° C |
|---|---|---|
| Concentration for inhibiting activity of acetyl cholinesterase in the head of a house fly | $9.0 \times 10^{-7}$ M | $1.4 \times 10^{-5}$ M |
| $LD_{50}$ to house fly (addition of piperinyl butoxide) | 1.25 μg/g | 12.5 μg/g |
| $LD_{50}$ to larva of mosquito | 1.0 ppm | >10 ppm |

Having generally described the invention, a more complete understanding can be obtained by reference to certain specific experiments and examples, which are provided herein for purposes of illustration only and are not intended to be limiting unless otherwise specified.

EXPERIMENT 1

Treatment in water

Test Method:

In Wagner pots having 1/10,000 are area, Alluvium loam soil was filled. Germinated rice seeds and barnyard grass seeds were sowed, and were grown in a condition of 1 cm depth of water. When barnyard grasses were grown to the 3 – 3.5 leaf stage, the depth of water was varied to 3 cm and the specific amounts of the active ingredients shown in Table 2 were added to the water. After 30 days, the phytotoxicity to rice plants and the herbicidal effect to barnyard grass were observed. The results are shown in Table 2. In the tables, the ratings are as follows:

| Herbicidal effect | | Phytotoxicity of rice | |
|---|---|---|---|
| 5 | complete control | X | killed |
| 4 | excellent effect | ++++ | serious damage |
| 3 | large effect | +++ | high damage |
| 2 | fair effect | ++ | middle damage |
| 1 | small effect | + | low damage |
| 0 | no effect | ± | quite low damage |
| | | − | no damage |

Plants used for the test Rice variety:
Direct seeding paddy rice (Nihonbare) 2.5 – 3 leaf stage
Barnyard grass 3–3.5 leaf stage

TABLE 2

| | Herbicidal effect on barnyard grass | | | | Phytotoxicity of rice plant | | | |
|---|---|---|---|---|---|---|---|---|
| | α-NAC | | β-NAC | | α-NAC | | β-NAC | |
| DCPA | 2 g/a | 1 g/a | 2 g/a | 1 g/a | 2 g/a | 1 g/a | 2 g/a | 1 g/a |
| 50 g/a | 3 | 3 | 5 | 5 | ± | ± | − | − |
| 30 g/a | 3 | 3–4 | 5 | 5 | ± | ±∼+ | − | − |

In Table 2, it is clear that the combination of β-NAC with DCPA imparts special herbicidal selectivity to barnyard grass versus rice plants which is superior to that displayed by α-NAC. When β-NAC is combined with DCPA, the selective herbicidal effect can be attained by adding only 1 – 2 g/are which is a quite smaller amount than the conventional herbicides. This fact is considered to be caused by the physiological mechanism of an enzyme.

REFERENCE EXPERIMENT 2

Foliage treatment

Test Method

In unglazed pots having diameters of 9 cm, diluvium clay loam was filled and rice seeds and barnyard grass seeds were sowed and grown. When the rice was grown to the 2 – 3 leaf stage and barnyard grass was grown to the 3 – 4 leaf stage, 5 ml of predetermined concentrations of the active ingredients, as shown in Table 3, were sprayed onto the foliages by a spray gun. The phytotoxicity of rice and herbicidal effect on barnyard grass were observed 20 days from the treatment. The results are shown in Table 3.

TABLE 3

| | (Concentration of DCPA: 1000 ppm) | | | |
|---|---|---|---|---|
| | Herbicidal effect on barnyard grass | | Phytotoxicity of rice plant | |
| Concentration of NAC | α-NAC | β-NAC | α-NAC | β-NAC |
| 50 ppm | 5 | 5 | ++ | ++ |
| 10 ppm | 5 | 5 | + | + |

As is clear from Table 3, there was no substantial difference between the combination of α-NAC and DCPA and the combination of β-NAC and DCPA. Phytotoxicity to rice plants was found, though it was not found by an application of 1000 ppm of DCPA alone. As can be seen, a very significant difference between the results of a foliage treatment and a treatment in water exists.

EXPERIMENT 3

Decomposition of DCPA in soil:

The method of this invention is treatment in flooded water. Accordingly, transfer of the active ingredients into the soil of the paddy field is unavoidable. The decompositions of the active ingredients in the paddy soil were measured.

| Soil: | Alluvium loam soil |
|---|---|
| Amount: | DCPA: 100 g/are |
| | α-NAC 3.3 g/are |
| | β-NAC 3.3 g/are |
| The active ingredients were uniformly mixed in a 5 mm thickness. | |
| Analysis: | The concentrations of DCPA were measured by gas chromatography in time intervals. |
| Results of minimum residues: | |
| DCPA only | 4 days |
| Combination of DCPA and α-NAC | 10 days |
| Combination of DCPA and β-NAC | 20 days |

Both α-NAC and β-NAC inhibit the decomposition of DCPA and β-NAC had higher effect for inhibiting the decomposition of DCPA. The results may bear a close relation with the effect of the invention.

The method of the invention can be performed by applying the active ingredients in the form of an emulsion, a wettable powder, granules, pellet and other suitable forms. It is possible to prepare the composition of this invention by conventional preparative techniques for agrochemicals by using desirable inert carriers. The carriers include liquid carriers such as xylene, isophorone, cyclohexanone, methyl naphthalene, diethyl formamide and the like and solid carriers such as bentonite, talc, kaoline, clay, diatomaceous earth and the like. It is also possible to add various emulsifiers, dispersing agents, wetting agents and the like in desirable proportions.

Preparation of Granules 10 wt. parts of DCPA, 0.4 wt. part of β-NAC, 50 wt. parts of bentonite and 34.4 wt. parts of talc were mixed and crushed. 5 wt. parts of a dispersing agent (Sorpol 5060 manufactured by Toho Chemical Co.) was admixed with the mixture. The mixture was granulated by a granulating machine.

As is clear from the above discussion, this invention makes it possible to decrease the amount of DCPA needed for a herbicidal effect and to increase the leaf stage of barnyard grass which can be controlled as compared with the case of Japanese Patent Publication No. 16934/1974. Also, since β-NAC has a low insecticidal effect, the ecospecies in the environment are not disturbed. This is also one of the advantages of the invention.

EXAMPLE 1

Usual transplanting culture

DCPA and β-NAC were separately crushed into fine powders by a jetmizer. The crushed DCPA and β-NAC were mixed in ratios of 80 : 1; 40 : 1; 20 : 1 and 10 : 1 together with a dispersing agent (Sorpol 5039 manufactured by Toho Chemical Co. and Rapizol BB-74 manufactured by Nippon Fat & Oil Co.) to form a wettable powder. The compositions were applied under the following conditions in a paddy field of Ishigakijima, Okinawa-Ken, Japan.

1. Test Method:
   1. Plot size: Two replications, each 1 m² per division
   2. Culturing method: Usual transplanting
   3. Rice variety: Taichu 65
   4. Transplanting time:
      Feb. 27, 1974
      5 – 6 leaf stage of rice plants at the transplanting;
      3 – 5 cm depth of water.
   5. Time for treatment:
      a. Treating time Mar. 16, 1974 (17 days after transplanting)
      b. Leaf stage
         2 – 2.5 leaf stage of barnyard grass
         7 – 8 leaf stage of rice
   6. Treating method:
      Each composition was diluted with 50 cc of water and the solution was poured in the rows by using a watering pot
   7. Weed species:
      Barnyard grass (*Echinochloa crusgalli*);
      Monochoria vaginalis (*Burm fil*) *Presl*;
      Dopatrium junceum (*Roxb*) *Hamilt*;
      Rotala indica (*Willd*) *koehne*;
      Elatine triandra *Schk*;
      Eleocharis acicularis *Roem et Schult*;
      Scirpus juncoides *Roxb*;
      Cyperus microira *Steud*;
      Zizania aquatia; and
      Spirogra arcla *Kulz*.
   8. Observation:
      After 3 weeks from the treatment, the herbicidal effect and the phytotoxicity were observed.
2. Results:
   The results are shown in Table 4.

TABLE 4

| Composition | | Herbicidal effect | | Phytotoxicty to rice plant |
| DCPA | β-NAC | barnyard grass | broadleaf weeds | |
| --- | --- | --- | --- | --- |
| 40 g/are | 4.0 g/are | 5 | 5 | + |
| " | 2.0 g/are | 5 | 5 | ± |
| " | 1.0 g/are | 5 | 5 | — |
| " | 0.5 g/are | 5 | 5 | — |
| 30 g/are | 3.0 g/are | 5 | 5 | + |
| " | 1.5 g/are | 5 | 5 | — |
| " | 0.75 g/are | 5 | 5 | — |
| " | 0.38 g/are | 4.5 | 4.5 | — |
| 20 g/are | 2.0 g/are | 5 | 5 | — |
| " | 1.0 g/are | 5 | 5 | — |
| " | 0.5 g/are | 4 | 4.5 | — |
| " | 0.25 g/are | 4.5 | 4 | — |
| 10 g/are | 1.0 g/are | 4 | 3 | — |
| " | 0.5 g/are | 4 | 3.5 | — |
| " | 0.25 g/are | 2 | 3 | — |
| " | 0.125 g/are | 2 | 2 | — |
| 60 g/are | none | 0 | 0 | — |
| none | 4.0 g/are | 0 | 0 | — |

As shown in Table 4, under the conditions of the tests, wherein the composition was poured into the flooded water by using a watering pot, the application of 60 g/are of DCPA or 4 g/are of β-NAC imparted no herbicidal effect to barnyard grass and broadleaf weeds. However, the application of the combinations of DCPA and β-NAC imparted effective herbicidal activity to completely wither the barnyard grass without phytotoxicity to the rice. A significant feature of this invention is to completely wither barnyard grass and other annual weeds.

EXAMPLE 2

Mechanical transplanting using young seedlings

The tests were conducted by using the compositions of Example 1 in the paddy field of Ishigakijima, Okinawa-Ken, Japan.

1. Test Method:
   1. Plot size: Two replications each 1 m² per division.

2. Culturing method: Mechanical transplanting using young seedlings
3. Rice variety: Nihonbare
4. Transplanting: Apr. 8, 1974
   2.3 – 3 leaf stage of rice at the transplanting;
5. Depth of water: 3 – 5 cm
6. Time for treatment:
   A. First treatment: Apr. 19, 1974
      (16 days after transplanting)
      2 – 2.5 leaf stage of barnyard grass
   B. Second treatment: Apr. 23, 1974
      (20 days after transplanting)
      3 – 3.5 leaf stage of barnyard grass.
7. Treating method:
   Each composition was diluted with 50 cc of water and the solution was poured in the rows by using a watering pot.
8. Weed species:
   Barnyard grass (*Echinochloa crusgalli*);
   *Monochoria vaginalis* (*Burm fil*) *Presel*;
   *Rotala indica* (*Willd*) *Koehne*;
   *Scirpus juncoides Roxb*; and
   *Zizania aquatica*
9. Observation:
   After 20 days from the treatment (the first treatment and the second treatment), the herbicidal effects and the condition of the rice were observed.
2. Results:
   The results are shown in Table 5. The ratings are the same as in Example 1.

TABLE 5

| Composition | | | | A Herbicidal Effect | | A Phytotoxicity | | B Herbicidal Effect | | B Phytotoxicity | |
|---|---|---|---|---|---|---|---|---|---|---|---|
| DCPA | | β-NAC | | BG | BLW | N | T | BG | BLW | N | T |
| 40 g/are | | 0.5 | g/are | 5 | 5 | — | — | 2 | 2 | — | — |
| 30 | | 3.0 | | 5 | 5 | — | — | 5 | 5 | — | — |
| " | | 1.5 | | 5 | 5 | — | — | 5 | 5 | — | — |
| " | | 0.75 | | 5 | 5 | — | — | 5 | 4.5 | — | — |
| " | | 0.38 | | 5 | 4.5 | — | — | 3 | 2 | — | — |
| 20 | | 2.0 | | 5 | 5 | — | — | 4 | 4 | — | — |
| " | | 1.0 | | 5 | 5 | — | — | 3 | 2 | — | — |
| " | | 0.5 | | 4.5 | 4 | — | — | 0 | 0 | — | — |
| " | | 0.25 | | 4 | 4 | — | — | 0 | 0 | — | — |
| 60 | | none | | 0 | 0 | — | — | 0 | 0 | — | — |
| none | | 4.0 | | 0 | 0 | — | — | 0 | 0 | — | — |

Note:
BG: barnyard grass
BLW: broadleaf weeds
N: Nihonbare
T: Taichu 65

As is clear from Table 5, when the compositions were poured into the flooded water by using a watering pot at 2 – 2.5 leaf stage and 3 – 3.5 leaf stage of barnyard grass, no herbicidal effect was found by application of 60 g/are of DCPA. However, remarkable herbicidal effect was found by the combination of DCPA with a small amount of β-NAC. In spite of the young seedling transplant culturing, phytotoxicity to the rice plants was not found. Selective and significant herbicidal effects were achieved by the combinations of this invention under the conditions of the test. As shown in Table 5, the optimum amounts of the active ingredients are about 30 g/are of DCPA and about 1.5 g/are of β-NAC. In accordance with the method of this invention, it is possible to completely control barnyard grass and other annual weeds by applying 30 g of DCPA and 1.5 g of β-NAC per 1 are at the 2 – 2.5 leaf stage of barnyard grass and even at the 3 – 3.5 leaf stage of barnyard grass. This has not been attained by the conventional methods.

Having now fully described the invention, it will be apparent to one of ordinary skill in the art that many changes and modifications can be made thereto without departing from the spirit or scope of the invention as set forth herein.

What is claimed as new and intended to be covered by Letter Patent is:

1. A method of removing annual weeds from a flooded paddy rice field which comprises applying to the flooded water from 20–50 g/are of 3,4-dichloropropionanilide and 0.2 – 2.5 g/are of β-naphthyl-N-methyl carbamate.

2. The method of removing annual weeds of claim 1, wherein the composition of 3,4-dichloropropionanilide and β-naphthyl-N-methyl carbamate is applied in the form of granules into the flooded water.

3. The method of removing annual weeds of claim 1, wherein 3,4-dichloropropionanilide and β-naphthyl-N-methyl carbamate are applied at rates of 25 – 35 g/are of 3,4-dichloropropionanilide and 1.0 – 1.7 g/are of β-naphthyl-N-methyl carbamate.

4. The method of claim 1, wherein the annual weeds are barnyard grass in the 3 – 3.5 leaf stage.

5. The method of claim 1, wherein the β-naphthyl-N-methyl carbamate is first added to the water and then the 3,4-dichloropropionanilide is added less than two days later.

6. The method of claim 1, wherein the flooded water is 3 – 6 cm deep.

7. A method of removing annual weeds in a flooded paddy field which comprises adding 30 g per 1 are of 3,4-dichloropropionanilide to the flooded water, and then less than 2 days later adding to the water 1.5 g per 1 are of β-naphthyl-N-methyl carbamate without a foliage treatment.

* * * * *